United States Patent [19]

Ebeling et al.

[11] Patent Number: 4,800,161

[45] Date of Patent: Jan. 24, 1989

[54] PROCESS FOR THE MICROBIOLOGICAL PREPARATION OF ALDOSE-1-EPIMERASE

[75] Inventors: Wolfgang Ebeling; Harald Metz, both of Bickenbach; Wolfgang Brummer, Alsbach; Gunter Schmid, Muhltal; Ulrich Behrendt, Bischøl/Obb., all of Fed. Rep. of Germany

[73] Assignee: Merck Patent Gesellschaft mit beschrankter Haftung, Darmstadt, Fed. Rep. of Germany

[21] Appl. No.: 772,979

[22] Filed: Sep. 5, 1985

[30] Foreign Application Priority Data

Sep. 5, 1984 [DE] Fed. Rep. of Germany ....... 3432570

[51] Int. Cl.$^4$ .......................... C12N 9/90; C12N 1/20
[52] U.S. Cl. .................................. 435/233; 435/814; 435/822; 435/252.1
[58] Field of Search ................. 435/4, 14, 25, 26, 253, 435/822, 814

[56] References Cited

U.S. PATENT DOCUMENTS 3,912,592 10/1975 Makover et al. .................... 435/822
3,964,974 7/1976 Banauch et al. ....................... 435/26

FOREIGN PATENT DOCUMENTS 0024206 2/1981 European Pat. Off. .

OTHER PUBLICATIONS van Schie (1984) FEMS Microbiology Letters, vol. 24, pp. 133–138.
Manual of Clinical Microbiology, 3rd ed. (1980). American Society for Microbiology, Washington, D.C., pp. 269–271.
Bergey's Manual of Determinative Bacteriology, 8th ed. (1974).
The Williams & Wilkins Co., Baltimore, pp. 436–438.
Gatz et al. (1986) Nucleic Acid Research, vol. 14, No. 10, pp. 4309–4323.
Bentley et al. (1960) The Journal of Biological Chemistry, vol. 235, No. 5, pp. 1219–1224.
Kinoshita et al. (1981) Biochemica et Biophysica Acta, vol. 662, pp. 285–290.
Bailey et al. (1975) in Methods in Enzymology, pp. 471–493.
Fruton, Joseph S., "General Biochemistry", Second Edition.

Primary Examiner—Robert J. Warden
Assistant Examiner—Jack Spiegel
Attorney, Agent, or Firm—Millen & White

[57] ABSTRACT

The invention relates to a process for the microbiological preparation of aldose-1-epimerase by cultivating microorganisms in a nutrient medium and release of the enzyme from the cells, which process is characterized in that microorganisms of the genus Acinetobacter are used.

7 Claims, No Drawings

PROCESS FOR THE MICROBIOLOGICAL PREPARATION OF ALDOSE-1-EPIMERASE

BACKGROUND OF THE INVENTION

The invention relates to a process for the microbiological preparation of aldose-1-epimerase (mutarotase) by cultivating a microorganism, suitable for the formation of this enzyme, of the genus Acinetobacter.

Mutarotase (EC 5.1.3.3) accelerates the establishment of equilibrium between the α- and β-anomers of aldohexoses, for example between α- and β-glucose or α- and β-galactose. The main application of the enzyme is in analytical biochemistry for the acceleration of enzymatic detection reactions for aldoses by means of enzymes specific for the α- or β-form, where the establishment of equilibrium between the two anomers is the rate-determining step, for example in determination methods with glucose-dehydrogenase, glucose-oxidase, galactose-dehydrogenase or galactose-oxidase. Such determinations are conventional and are described in U.S. Pat. No. 3,964,974 and Anal. Biochem. 43. 312 (1971), which disclosure is incorporated by reference herein. A large-scale industrial application could become a interest, for example, for the glucoamylase/-glucose-isomerase process, because glucoamylase releases β-glucose which can be converted by the glucose-isomerase only after mutarotation to the α-form.

Mutarotase is very widespread in nature. It occurs in various microorganisms (bacteria, yeasts, thread fungi), in plants and in animal tissues.

Significant enzyme contents which allow isolation of mutarotase on an industrial scale have so far been found only in the kidneys of mammals (cattle, pigs); all the known commercial products are prepared from kidneys. It is known from Bailey, Meth. Enzymol. 1975, page 478, that bovine kidneys contain more than 60 times the activity per g of fresh weight than, for example, Escherichia coli. In Biochim. Biophys. Acta 662, 285 (1981), a process for the microbiological preparation of mutarotase from strains of Aspergillus niger is described for the first time. According to this, a mutarotase activity of 4.4 mU/ml of culture broth was obtained from the best strain, the Michaelis constant was 50 mM, and the pH optimum was in the range 5-7.

However, the known microbial process has a very low yield as compared with the preparation process for mutarotase from bovine kidneys. In addition, the characteristics of the enzyme from Aspergillus niger are very unfavorable for the establishment of equilibrium in enzymatic determinations of aldoses.

SUMMARY OF THE INVENTION

One object of the invention is to provide a process for the microbiological preparation of aldose-1-epimerase (mutarotase) having an activity and consequently an enzyme yield comparable with those of mutarotase obtained from mammal kidneys. Additional objects include providing a process as above wherein the activity formed is preserved in the cells for the longest possible time and with maximum stability; wherein the enzyme formed has favorable properties with respect to optimum substrate concentration, stability and pH optimum; and wherein interfering foreign activities or other impurities in the crude extracts are as low as possible or are easily separable.

Upon further study of the specification and appended claims, further objects and advantages of this invention will become apparent to those skilled in the art.

These objects are achieved by providing a process according to the invention for the microbiological preparation of aldose-1-epimerase, wherein a microorganism, from the genus Acinetobacter and capable of forming aldose-1-epimerase, is cultivated in a nutrient medium, and the enzyme is separated off after release from the cell. Preferred microorganisms are those of the strains Acinetobacter calcoaceticus DSM 30,007, DSM 30,008, DSM 30,010 or DSM 30,011 and their mutants or variants.

All species of the genus Acinetobacter as described in Bergey's Manual of Determinative Bacteriology, 8th Ed., Baltimore 1974, pp 437–438, and all strains of the preferred calcoaceticus species will be operable in the process of this invention at least to a finite degree. Further preferred strains are for example ATCC 15 567, ATCC 23 055, ATCC 23 221 or ATCC 23 237 and their mutants or variants.

DETAILED DISCUSSION

In comparison with the mutarotase prepared by the known processes, a number of further advantages arise, in addition to the extreme increase in yield up to 1,000 mU/ml of culture broth: Bacterial starting material can be prepared at any time in any desired quantity, so that there are no problems such as are encountered in the procurement and storage of large quantities of organs; the concentration and purification of mutarotase from crude bacteria extracts up to a degree of purity applicable for diagnostic purposes is possible by simpler, more effective and less expensive processes than in the production from organs. Like the mutarotase obtained from bovine kidneys and from Aspergillus niger, the mutarotase prepared according to the invention also has a high pH stability and temperature stability and can be lyophilised without problems. In addition, however, the mutarotase prepared according to the invention has some characteristic advantages which have a favorable effect on the use in the glucose determination system: as compared with mutarotase from bovine kidneys ($K_M$=18–20 mM) and that from Aspergillus niger ($K_M$=50 mM), the mutarotase according to the invention has a Michaelis constant ($K_M$=6–8 mM) which is smaller by a factor of 3 or 8 respectively. Precisely in the suboptimal substrate range in which measurements are made in a glucose determination, the higher affinity of the bacterial enzyme has a positive effect. For galactose, the mutarotase from Acinetobacter has a Michaelis constant which is 3 times that of the mutarotase from bovine kidneys, that is to say there is less interference by galactose relative to glucose with the activity of the mutarotase from Acinetobacter in the suboptimal range than in the case of the enzyme from bovine kidneys.

Compared with the mutarotase from bovine kidneys and from Aspergillus niger, that from Acinetobacter has a pH optimum which is shifted somewhat further towards the alkaline region (pH 7–8). This has the consequence that, in a glucose determination (pH 7.6), the pH optima of the glucose-dehydrogenase and of the mutarotase are mutually matched even better and excellently complement each other. The mutarotase from Acinetobacter shows an even more pronounced independence from SH-protective reagents than the mutarotase from bovine kidneys. Since the glucose-dehydrogenase does not require SH protection, the two enzymes employed for the glucose determination complement each other in an extraordinary way even on this point.

As a strongly basic protein, the mutarotase according to the invention is readily bonded to cation exchangers, which leads to improved and simplified purification. The product obtained by this process contains less interfering accompanying substances, such as pigments, foreign enzymatic activities (LDH, substances which activate NADH-oxidase) and substances which can lead to turbidity and flocculation in the later use of the mutarotase as a constituent of reagent solutions.

The microorganisms are cultured as slant agar cultures on conventional nutrient media which contain, for example, meat extract, peptones and/or yeast extract and/or inorganic salts and additional C sources. For further propagation of the organisms, shaken or standing cultures in appropriate nutrient solutions can be cultivated by the submerged process. The cultures are started between 20° and 40° C., preferably at 25°–36° C. Using a well-grown culture of an age of about 5 to 36 hours, fermenters can be inoculated which can contain, for example, a nutrient solution based on yeast extract, cornsteep, peptone and/or mineral salts and, if appropriate an additional carbon source. Suitable additional carbon sources are carboxylic acids, such as lactic acid, citric acid or acetic acid, or also glucose, fructose, sucrose, galactose, xylose, glycerol, 2,3-butanediol, ethanol and preferably lactic acid and/or citric acid. The starting pH of the culture should preferably be between 6.0 and 8.0. For inoculation of the nutrient solution, inoculation quantities of 0.1%–10% of the culture volume can be used. The cultivation can be carried out either by the batch process or partially or fully continuously in one or more stages.

After the activity maximum has been reached, the cells are separated off by centrifugation or other suitable methods and the enzyme-containing phase is then cooled down. The intracellular mutarotase is released by lysozyme digestion in the case of small quantities of bacteria and, in the case of larger working volumes, by mechanical cell digestion, for example by means of a high-pressure homogeniser or glass bead mills, by osmotic treatment of the cells or by other suitable processes for releasing intracellularly formed bacterial enzymes. For industrial purposes, it is also possible to use the cells obtained instead of the released enzyme.

The slurry of bacteria is as a rule digested, with cooling and in the presence of a detergent, by high-pressure treatment with the aid of a high-pressure homogenizer. The bacteria fragments are separated off as far as possible by centrifuging or other suitable methods. Accompanying substances can be precipitated from the cloudy supernatant liquor by means of precipitating agents, such as ammonium sulphate or polyethylene glycol. After a subsequent dialysis, the enzyme can be directly adsorbed on a cation exchanger. The dialysis of the cloudy enzyme solution is preferably carried out by ultra-filtration with tubular membrane modules. The enzyme is adsorbed from a weakly acidic medium on the ion exchanger which is introduced in the dry form into the enzyme solution. The loaded exchanger is washed on a suction filter until the wash water is clear. It is then packed into a chromatography column and the mutarotase is eluted with a potassium chloride gradient and then lyophilised.

By the process according to the invention, a mutarotase can be isolated which is characterised by the following properties: the molecular weight is about 80,000 d (4 sub-units of 20,000 d each), the pH activity optimum is in the pH range from 7 to 8, and the temperature optimum is at 42° C. to 46° C. The Michaelis constant for glucose is 6–8 mM.

The activity of the mutarotase was stable over a period of half a year at 4° C., 25° C. and also 30° C. and at pH values of 6.7–8.4. Lyophilisation is possible without problems and without any significant activity losses.

The activity of the mutarotase prepared according to the invention depends on the presence of free sulfydryl groups which can be blocked by SH-reagents such as N-ethylmaleimide, 5,5'-dithio-bis-(2-nitrobenzoic acid) and iodoacetate. Special SH-protection in diluent and test buffers is, however, not necessary. At concentrations of 2 mM, $Hg^{++}$ and $Fe^{+++}$ ions reduce the activity to about half; $Cu^{++}$, $Co^{+++}$ and $Zn^{++}$ ions are complete inhibitors in the same concentration.

The mutarotase is specific to aldohexoses. The conversion rate for galactose is 3.5 times higher than that for glucose at the same Michaelis constant. The Michaelis constant for glucose is 6–8 mM.

The determination of activity is carried out as follows:

Principle:

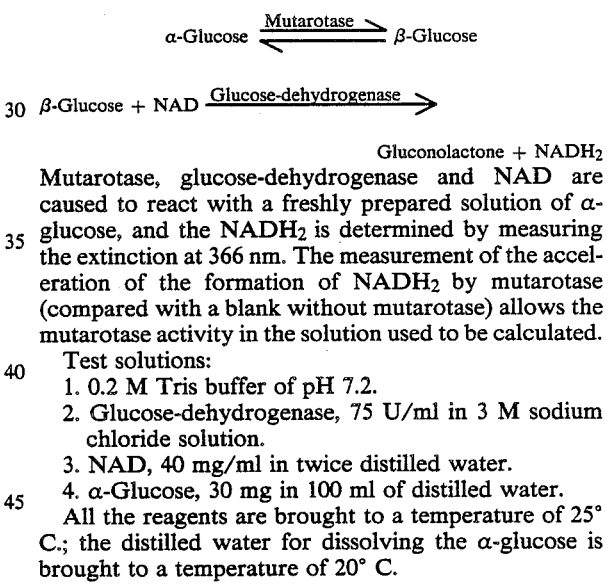

Gluconolactone + $NADH_2$

Mutarotase, glucose-dehydrogenase and NAD are caused to react with a freshly prepared solution of α-glucose, and the $NADH_2$ is determined by measuring the extinction at 366 nm. The measurement of the acceleration of the formation of $NADH_2$ by mutarotase (compared with a blank without mutarotase) allows the mutarotase activity in the solution used to be calculated.

Test solutions:
1. 0.2 M Tris buffer of pH 7.2.
2. Glucose-dehydrogenase, 75 U/ml in 3 M sodium chloride solution.
3. NAD, 40 mg/ml in twice distilled water.
4. α-Glucose, 30 mg in 100 ml of distilled water.

All the reagents are brought to a temperature of 25° C.; the distilled water for dissolving the α-glucose is brought to a temperature of 20° C.

|  | Analysis | Blank |
|---|---|---|
| Solution 1 | 1.00 ml | 1.00 ml |
| Solution 2 | 0.10 ml | 0.05 ml |
| Solution 3 | 0.05 ml | 0.05 ml |
| Mutarotase solution | 0.10 ml | — |
| Twice distilled $H_2O$ | — | 0.10 ml |

As soon as the extinction is constant, the start is made with 0.10 ml of solution 4 in each case.

A fresh glucose solution is prepared for each measurement. It is absolutely necessary to adhere to the following procedure in order to allow for the existing mutarotation: a 150 ml beaker is filled with 100 ml of distilled water and the temperature is adjusted to 20° C. The beaker is evenly stirred, 30 mg of α-glucose are added, the stopwatch is started and the time is marked on the recorder chart. Mixing takes place for 30 seconds. Within the next 15 seconds, the glucose solution is pipetted into the cell, the cell content is thoroughly mixed and, after the expiration of these 15 seconds, the increase in extinction is recorded. The measurement is taken at 366 nm, layer thickness 1 cm, cell temperature 25° C.

For evaluation, a tangent is put to the linear part at the origin of the recording curve, and ΔE/minute is read off; subtraction of the blank from the analysis value gives a value of ΔΔE/minute, which is inserted into the following calculation equation:

Enzyme activity = ΔΔE/minute × 4.09 U of mutarotase per ml of enzyme solution employed Crude mutarotase samples are to be tested for freedom from glucose, since the β-glucose fraction introduced interferes with the test.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

In a fermenter, 100 liters of a sterile nutrient solution of the following composition

| | |
|---|---|
| Peptone from casein | 0.5% |
| Yeast extract | 1.0% |
| Cornsteep powder | 0.3% |
| Dipotassium hydrogen phosphate | 0.8% |
| Magnesium sulphate heptahydrate | 0.04% |
| Glucose | 1.2% |
| Silicone antifoam | 20 ml |
| pH value | 6.8 | are inoculated with 1 l of an 13 hours old submerged culture of Acinetobacter calcoaceticus M 30,007, which had been cultured in the same nutrient solution.

This culture is incubated for 18 hours at moderate aeration (stirrer: 250 rpm, air: 60 l/minute, gauge pressure: 0.5 bar) and at 34° C.

During the first 2-10 hours, the cell mass, measured as turbidity, increases and then remains constant. After 10 hours, the culture has reached its maximum of mutarotase activity at 340 U/l after 10 hours.

The release of the mutarotase from the bacteria and the activity determination are carried out by the following method.

3 ml of a thoroughly mixed, glucose-free fermenter sample are centrifuged off for 10 minutes at 5,000 rpm and the supernatant liquor is discarded. The bacteria mass is suspended in 3 ml of 0.1 M phosphate buffer of pH 6.5 and 0.1 ml of EDTA solution (1.8 g/l) and rapidly frozen in the centrifuge tube in an acetone/dry ice cold bath (about 15 minutes) and then thawed in a water bath of about 40° C. 1 drop of a detergent and 25-30 mg of lysozyme are added (about 15,000 U/mg) and the mixture is stirred from 15 minutes at 28° C. by means of a magnetic stirrer. To inactivate NADH oxidases, the mixture is then heated for 5 minutes to 45° C., digested and clarified by centrifugation (about 2 minutes). The enzyme is determined in the clear supernatant liquid.

EXAMPLE 2

Enzyme working-up 0.5% of a detergent and 0.1 mol/l of potassium chloride are added to 100 l of bacteria slurry. The cells are digested by means of a high-pressure homogeniser at 500 bar. While doing this, the bacteria slurry must be cooled. The cell fragments are separated off as far as possible by means of a centrifuge (3,000 × g; running time 3 hours). The residue is discarded, and 20% of polyethylene glycol are added to the cloudy centrifugate, in order to precipitate accompanying substances. The mixture is stirred for a further 30 minutes and the precipitate is centrifuged off. The still cloudy supernatant liquid contains about 2 U/ml of mutarotase and is subjected to diafiltration against water up to a connectivity of $3 \times 10^{-3}$ S. After the diafiltration, the mutarotase is adsorbed at pH 5.5 by a batch method on a dry ion exchanger. 5-10 g of exchanger are required for 20,000 units. The loaded exchanger is filtered off with suction and washed with 0.025 M potassium phosphate buffer of pH 5.5 until the filtrate is free of turbidity. The loaded exchanger is then packed into a column, washed with 0.025 M potassium phosphate buffer of pH 5.5 until free of extinction and then eluted with a potassium chloride gradient.

The enzyme-containing fractions are collected, concentrated to 60-100 U/ml by ultrafiltration and then lyophilised. The yield is 70%, and the specific activity is about 6.5 U/mg of protein.

EXAMPLE 3

The strain used is Acinetobacter calcoaceticus M 30,008. The culture method and the nutrient solution correspond to Example 1, with the exception that only 1% of glucose was initially introduced, while 3.5% of glucose were subsequently metered in continuously. The culture has reached its maximum of mutarotase activity at 490 U/l after 15 hours.

EXAMPLE 4

The strain used is Acinetobacter calcoaceticus M 30,010. The culture method and the nutrient solution correspond to Example 3, but the glucose is replaced by 1% of sodium lactate. During the growth, 20% lactic acid is titrated in as a function of the pH value, or it is metered in at constant rate and the pH value is regulated with ammonia to pH 6.8. The culture has reached its maximum of mutarotase activity at 1,200 U/l after 12 hours.

EXAMPLE 5

The cultivation is carried out analogously to Example 4, but 50% citric acid is used in place of lactic acid. After 10 hours, the cultivation is continued in the presence of an anionic, cationic or non-ionic surfactant, preferably N-cetylpyridinium chloride in a concentration of 0.01 to 0.1%. The maximum of mutarotase activity at 2,200 U/l is reached after 20 hours.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the microbiological preparation of aldose-1-epimerase comprising extracting and isolating said aldose-1-epimerase from a culture of a microorganism of the genus Acinetobacter.

2. A process for the microbiological preparation of aldose-1-epimerase, comprising cultivating a microorganism of the genus Acinetobacter in a nutrient medium, and subsequently releasing the aldose-1-epimerase from the resulting cells and isolating said aldose-1-epimerase.

3. A process according to claim 2, wherein the microorganism is Acinetobacter calcoaceticus.

4. A process according to claim 3, wherein the microorganism is a strain of Acinetobacter calcoaceticus DSM 30,007, DSM 30,008, DSM 30,010, DSM 30,011, ATCC 15 567, ATCC 23 055, ATCC 23 221 or ATCC 23 237.

5. A process according to claim 4, wherein the nutrient medium contains a carbon source which is lactic acid or citric acid.

6. A process according to claim 4, wherein the nutrient medium contains a carbon source which is glucose, fructose, sucrose, galactose or xylose.

7. A process according to claim 4, wherein the nutrient medium contains a carbon source which is glycerol, 2,3-butanediol or ethanol.

* * * * *